United States Patent
Pan et al.

(10) Patent No.: US 12,287,558 B2
(45) Date of Patent: Apr. 29, 2025

(54) NONLINEAR OPTICAL CRYSTAL OF GUANIDINIUM TETRAFLUOROBORATE, PREPARATION METHOD AND USE THEREOF

(71) Applicant: XINJIANG TECHNICAL INSTITUTE OF PHYSICS & CHEMISTRY, CHINESE ACADEMY OF SCIENCES, Xinjiang (CN)

(72) Inventors: Shilie Pan, Urumqi (CN); Miriding Mutailipu, Urumqi (CN); Ming Xia, Urumqi (CN); Jian Han, Urumqi (CN)

(73) Assignee: XINJIANG TECHNICAL INSTITUTE OF PHYSICS & CHEMISTRY, CHINESE ACADEMY OF SCIENCES, Urumqi (CN)

( * ) Notice: Subject to any disclaimer, the term of this patent is extended or adjusted under 35 U.S.C. 154(b) by 55 days.

(21) Appl. No.: 18/032,631

(22) PCT Filed: Dec. 22, 2021

(86) PCT No.: PCT/CN2021/140370
§ 371 (c)(1),
(2) Date: Apr. 19, 2023

(87) PCT Pub. No.: WO2022/135451
PCT Pub. Date: Jun. 30, 2022

(65) Prior Publication Data
US 2023/0383439 A1   Nov. 30, 2023

(30) Foreign Application Priority Data
Dec. 26, 2020 (CN) ......................... 202011568533.1

(51) Int. Cl.
*G02F 1/355* (2006.01)
*C07C 279/02* (2006.01)
(Continued)

(52) U.S. Cl.
CPC ............ *G02F 1/355* (2013.01); *C07C 279/02* (2013.01); *C30B 7/10* (2013.01); *C30B 29/54* (2013.01);
(Continued)

(58) Field of Classification Search
CPC ........ G02F 1/353; G02F 1/355; G02F 1/3551; C30B 7/10; C30B 29/54; C07B 2200/13; C07C 279/02
See application file for complete search history.

(56) References Cited

U.S. PATENT DOCUMENTS 10,564,514 B1 *   2/2020   Pan ...................... C30B 11/003

FOREIGN PATENT DOCUMENTS

| CN | 103205811 A | 7/2013 |
| CN | 106745022 A | 5/2017 |
| CN | 112760717 A | 5/2021 |

OTHER PUBLICATIONS

Mar. 1, 2022 International Search Report issued in International Patent Application No. PCT/CN2021/140370.
(Continued)

*Primary Examiner* — Daniel Petkovsek
(74) *Attorney, Agent, or Firm* — Oliff PLC

(57) ABSTRACT

A nonlinear optical crystal of guanidinium tetrafluoroborate has a chemical formula of $[C(NH_2)_3]BF_4$ and a molecular weight of 146.89, belongs to the trigonal crystal system, has a space group of R3m; has lattice parameters of a=7.4634 (10)Å, b=7.4634(10)Å, c=9.1216(19) (6)Å, and Z=3; has an ultraviolet cutoff edge of 200 nm; and has a frequency-multiplication response that is 4-5 times that of the commercialized nonlinear optical crystal KDP. A hydrothermal method, a room-temperature solution method, an evaporation method or a solvothermal method is used to grow the crystal in a centimeter-scaled size. The crystal can produce
(Continued)

frequency-doubling, frequency-tripling, frequency-quadrupling, frequency-quintupling or frequency-sextupling harmonic light output from the fundamental frequency light of 1064 nm generated by a Nd:YAG laser, and/or can produce ultraviolet and deep-ultraviolet frequency-multiplication light output below 200 nm.

7 Claims, 2 Drawing Sheets

(51) Int. Cl.
    *C30B 7/10*           (2006.01)
    *C30B 29/54*         (2006.01)
    *G02F 1/35*          (2006.01)

(52) U.S. Cl.
    CPC ............ *G02F 1/353* (2013.01); *G02F 1/3551* (2013.01); *C07B 2200/13* (2013.01)

(56) References Cited

OTHER PUBLICATIONS

Marek Szafrański. "Effect of High Pressure on the Supramolecular Structures of Guanidinium Based Ferroelectrics". CrystEngComm, vol. 16, May 19, 2014, pp. 6250-6256.

S. Haussühl. "Pyroelectric, Dielectric, Piezoelectric, and Elastic Properties of Trigonal Guanidinium Tetrafluoroborate, C(NH2)3BF4". Zeitschrift für Kristallographie, vol. 187, 1989, pp. 153-158.

Min Luo et al. "Rational Design of the Metal-Free KBe2BO3FR2—(KBBF) Family Member C(NH2) 3SO3F With Ultraviolet Optical Nonlinearity". Angew. Chem. Int. Ed., 2020, vol. 59, p. 15978-15981.

Wang et al., "Czochralski and Flux Growth of Crystals for Lasers and Nonlinear Optics", Handbook of Crystal Growth, Ch. 5, pp. 169-208, 2015.

Perlov et al., "Isothermal growth of B-barium metaborate single crystals by continuous feeding in the top-seeded solution growth configuration", Journal of Crystal Growth, 137, pp. 123-127, 1994.

Loiacono et al., "Growth of KH2PO4 crystals at constant temperature and supersaturation", Journal of Crystal Growth, 62, pp. 545-556, 1983.

Chen et al., "Nonlinear Optical Borate Crystals: Principles and Applications", 2012.

Zyss et al., "Relations between microscopic and macroscopic lowest-order optical nonlinearities of molecular crystals with one- or two-dimensional units", The American Physical Society. Physical Review A, vol. 26, No. 4, pp. 2028-2048, Oct. 1982.

Wu et al., "Absorpton-Edge Calculations of Inorganic Nonlinear Optical Crystals", Applied Physics A: Solids and Surfaces, 54, pp. 209-220, 1992.

Chen et al., "Design and synthesis of an ultraviolet-transparent nonlinear optical crystal Sr2Be2B2O7", Nature, vol. 373, Letters to Nature, pp. 322-324, Jan. 1995.

\* cited by examiner

NONLINEAR OPTICAL CRYSTAL OF GUANIDINIUM TETRAFLUOROBORATE, PREPARATION METHOD AND USE THEREOF

CROSS-REFERENCE TO RELATED APPLICATIONS

This application claims priority of Chinese patent application No. 202011568533.1 filed on Dec. 26, 2020, which is fully incorporated herein by reference.

TECHNICAL FIELD

The invention relates to a nonlinear optical crystal of guanidinium tetrafluoroborate with a molecular formula of [C(NH$_2$)$_3$]BF$_4$, which is used in infrared-visible-ultraviolet-deep ultraviolet spectral region, a preparation method and use thereof. It belongs to the technical fields of crystal materials and optics.

BACKGROUND ART

With the strong demand for deep ultraviolet laser sources (generally referred to as wavelengths shorter than 200 nm) by 193 nm photolithography technology, micro-nano fine laser processing, and modern instruments such as ultra-high energy resolution photoelectron spectroscopy and photoelectron emission microscopes, etc., the development of all-solid-state deep ultraviolet laser source has become a hot spot of recent research in the global laser science community. To develop all-solid-state deep ultraviolet laser source, deep ultraviolet nonlinear optical crystal is a very critical component.

Ultraviolet—and deep ultraviolet—nonlinear optical crystals currently used in the industry mainly include LiB$_3$O$_5$(LBO), CsB$_3$O$_5$(CBO), CsLiB$_6$O$_{10}$ (CLBO), BaB$_2$O$_4$(BBO) and KBe$_2$BO$_3$F$_2$(KBBF) crystals. The LBO crystal has a wide light transmission range, high optical uniformity, a larger effective frequency-multiplication factor (3 KDP) and a high damage threshold (18.9GW/cm$^2$). However, due to its relatively low birefringence ($\Delta$n=0.04-0.05), it cannot achieve phase matching in the deep ultraviolet region, and its shortest frequency-multiplication wavelength is 276 nm. Similar to LBO crystals, CBO and CLBO crystals also have relatively low birefringence, which significantly limited their application in the deep ultraviolet region. BBO crystal, although having a larger frequency-multiplication factor and higher birefringence, has the shortest frequency-multiplication wavelength of 204.8 nm due to its relatively higher ultraviolet absorption cut-off edge (189 nm), which limits its application in the deep ultraviolet region. KBBF, although capable of conducting the frequency-sextupling output directly to the fundamental frequency light of 1064 nm, is difficult to grow into a large sized crystal due to its layered growth habit, which limits its application to a certain extent. Therefore, it is urgent to develop new deep ultraviolet nonlinear optical crystals with excellent comprehensive properties.

SUMMARY OF THE INVENTION

The object of the present invention is to provide a nonlinear optical crystal of guanidinium tetrafluoroborate. The crystal has a chemical formula of [C(NH$_2$)$_3$]BF$_4$ and a molecular weight of 146.89. It belongs to the trigonal crystal system; its space group is R3m; its lattice parameters are a=7.4634(10)Å, b=7.4634(10)Å, c=9.1216(19) (6)Å, Z=3; its ultraviolet cut-off edge is below 200 nm; and its frequency-multiplication response is 4-5 times of that of commercial nonlinear optical crystal KDP. The crystal has high laser damage threshold and moderate hardness; can be processed easily; is stable and not deliquescent easily in air.

Another object of the present invention is to provide a method for preparing said nonlinear optical crystal of guanidinium tetrafluoroborate.

Another object of the present invention is to provide use of said nonlinear optical crystal of guanidinium tetrafluoroborate.

The nonlinear optical crystal of guanidinium tetrafluoroborate according to the present invention has a chemical formula of [C(NH$_2$)$_3$]BF$_4$ and a molecular weight of 146.89. It belongs to the trigonal crystal system; its space group is R3m; its lattice parameters are a=7.4634(10)Å, b=7.4634(10)Å, c=9.1216(19) (6)Å, Z=3; and its ultraviolet cut-off edge is below 200 nm.

The method for preparing the nonlinear optical crystal of guanidinium tetrafluoroborate adopts hydrothermal method, room temperature solution method, evaporation method or solvothermal method to generate the crystal; said hydrothermal method for preparing the nonlinear optical crystal of guanidinium tetrafluoroborate is carried out by the specific operation steps of:

a. mixing NH$_2$ group-containing compound and BF$_4$ group-containing compound in a molar ratio of NH$_2$:BF$_4$=3:1, and fully grinding the compounds, then adding 10-50 mL of deionized water to mix and dissolve the compounds thoroughly;
wherein the NH$_2$ group-containing compound is guanidinium carbonate, guanidinium sulfate, guanidinium nitrate or guanidinium phosphate, and the BF$_4$ group-containing compound is tetrafluoroboric acid, ammonium tetrafluoroborate, lithium tetrafluoroborate or sodium tetrafluoroborate;

b. transferring the mixture solution of the step a into the polytetrafluoroethylene lining of an autoclave reactor with a volume of 25-100 mL, and sealing the reactor tightly;

c. placing the autoclave reactor of step b in an incubator, and heating up the incubator to 50-230° C. at a rate of 20-60° C./h, keeping the incubator at the temperature constantly for 3-15 days, and then reducing the temperature to room temperature at a cooling rate of 10-100° C./day;

d. opening the autoclave reactor, and obtaining a centimeter-scale large-size nonlinear optical crystal of guanidinium tetrafluoroborate in a colorless clear solution;

said room temperature solution method for preparing the nonlinear optical crystal of guanidinium tetrafluoroborate is carried out by the specific operation steps of:

a. mixing NH$_2$ group-containing compound and BF$_4$ group-containing compound in a molar ratio of NH$_2$:BF$_4$=3:1, fully grinding the compounds, then adding 10-200 mL deionized water to mix and dissolve the compounds thoroughly;
wherein the NH$_2$ group-containing compound is guanidinium carbonate, guanidinium sulfate, guanidinium nitrate or guanidinium phosphate, and the BF$_4$ group-containing compound is tetrafluoroboric acid, ammonium tetrafluoroborate, lithium tetrafluoroborate or sodium tetrafluoroborate;

b. transferring the mixture solution of step a into a beaker with a volume of 50-300 mL, conducting an ultrasonic treatment to make it fully mixed and dissolved, adjusting pH value of the solution to 1-11, filtering the solution through qualitative filter paper, and then sealing it with polyvinyl chloride film, placing it in a static environment with no shaking, no pollution, and no air convection, poking a number of small holes on the seal to adjust the volatilization rate of the solvent in the solution, and keeping it at room temperature until the growth ends, then obtaining nonlinear optical crystal of guanidinium tetrafluoroborate in a size of 1-20 mm$^3$;

said evaporation method for preparing the nonlinear optical crystal of guanidinium tetrafluoroborate is carried out by the specific operation steps of:

a. mixing the $NH_2$ group-containing compound and the $BF_4$ group-containing compound in a molar ratio of $NH_2:BF_4=3:1$, fully grinding the compounds, then adding 10-200 mL deionized water to mix and dissolve the compounds thoroughly;

wherein the $NH_2$ group-containing compound is guanidinium carbonate, guanidinium sulfate, guanidinium nitrate or guanidinium phosphate, and the $BF_4$ group-containing compound is tetrafluoroboric acid, ammonium tetrafluoroborate, lithium tetrafluoroborate or sodium tetrafluoroborate;

b. transferring the mixture solution of step a into a beaker with a volume of 50-300 mL, conducting an ultrasonic treatment to make it fully mixed and dissolved, and filtering the solution through qualitative filter paper;

c. placing the beaker of step b in an incubator, and heating up the incubator to 50-120° C. at a rate of 5-10° C./h, keeping the incubator at the temperature constantly for 3-15 days until the growth ends, then obtaining nonlinear optical crystal of guanidinium tetrafluoroborate in a size of 1-20 mm$^3$;

said solvothermal method for preparing the nonlinear optical crystal of guanidinium tetrafluoroborate is carried out by the specific operation steps of:

a. mixing the $NH_2$ group-containing compound and the $BF_4$ group-containing compound in a molar ratio of $NH_2:BF_4=3:1$, fully grinding the compounds, then adding 10-200 mL solvent to mix and dissolve the compounds thoroughly;

wherein the $NH_2$ group-containing compound is guanidinium carbonate, guanidinium sulfate, guanidinium nitrate or guanidinium phosphate; the $BF_4$ group-containing compound is tetrafluoroboric acid, ammonium tetrafluoroborate, lithium tetrafluoroborate or sodium tetrafluoroborate; and the solvent is deionized water, absolute ethanol, hydrofluoric acid or tetrafluoroboric acid;

b. transferring the mixture solution of step a into a beaker with a volume of 50-300 mL, conducting an ultrasonic treatment to make it fully mixed and dissolved, adjusting pH value of the solution to 1-11, filtering the solution through qualitative filter paper, and then sealing it with polyvinyl chloride film, placing it in a static environment with no shaking, no pollution, and no air convection, poking a number of small holes on the seal to adjust the volatilization rate of the solvent in the solution, and keeping it at room temperature until the growth ends, then obtaining nonlinear optical crystal of guanidinium tetrafluoroborate in a size of 1-20 mm$^3$.

Said nonlinear optical crystal of guanidinium tetrafluoroborate is used in the manufacture of multi-band frequency-multiplication devices or optical elements.

Said nonlinear optical crystal of guanidinium tetrafluoroborate is used in the preparation of producing frequency-doubling, frequency-tripling, frequency-quadrupling, frequency-quintupling or frequency-sextupling harmonic light output from the fundamental frequency light of 1064 nm generated by a Nd:YAG laser.

Said nonlinear optical crystal of guanidinium tetrafluoroborate is used in the preparation of producing a deep ultraviolet frequency-multiplication light output below 200 nm.

Said nonlinear optical crystal of guanidinium tetrafluoroborate is used in the manufacture of a frequency-multiplication generator, a frequency up or down converter, or an optical parametric oscillator.

The present invention relates to the nonlinear optical crystal of guanidinium tetrafluoroborate, preparation method and use thereof. Said crystal has the characteristics of high quality, large crystal size, good optical uniformity, etc.; meets the requirements for manufacturing devices; and can be widely used in infrared-visible-deep ultraviolet-deep ultraviolet wavebands.

Through the method for preparing the nonlinear optical crystal of guanidinium tetrafluoroborate according to the present invention, the nonlinear optical crystal of guanidinium tetrafluoroborate in a size of centimeter-scale is obtained, and no apparent layered growth habit is observed. By using a large-sized container and extending the growth period of the crystal, a large-sized nonlinear optical crystal of guanidinium tetrafluoroborate can be obtained correspondingly. Said nonlinear optical crystal can easily grow into a large and transparent crystal with no inclusion. This method has many merits such as fast growth speed, low cost, and easiness of obtaining crystals in a large size, etc.

Using the preparation method of nonlinear optical crystal of guanidinium tetrafluoroborate according to the present invention, large-sized nonlinear optical crystal is obtained. Based on the crystallographic data, the crystal blank is oriented and cut according to the required angle, thickness and section size.

By polishing its transparent surfaces, the crystal can be used as a nonlinear optical device. The nonlinear optical crystal of guanidinium tetrafluoroborate has a wider light transmission band, stable physical and chemical properties and high mechanical hardness; it is not frangible or deliquescent; and it can be cut, polished and preserved easily, etc.

SPECIFIC MODES FOR CARRYING OUT THE INVENTION

Example 1

Figure 1:
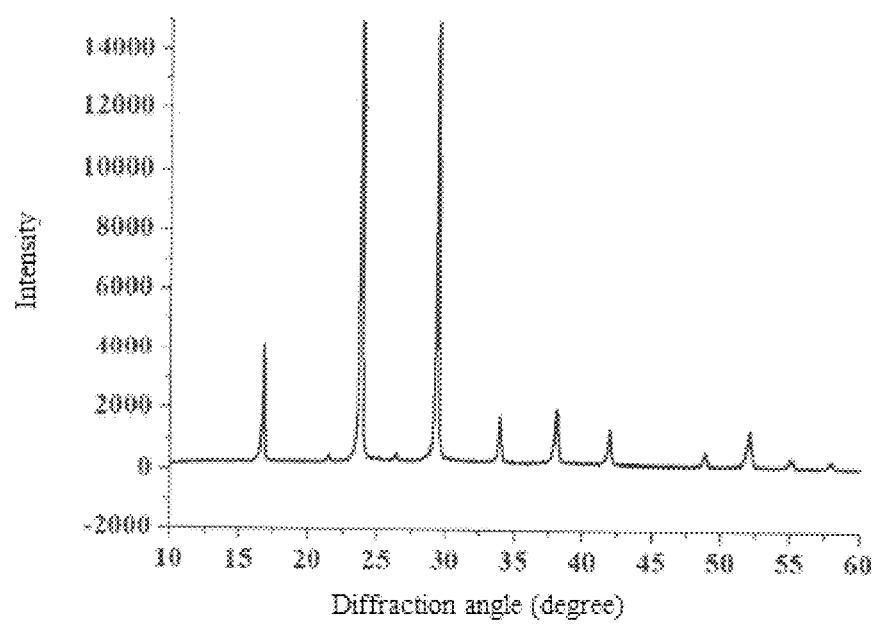
FIG. 1 is the XRD spectrum of the present invention, and the spectrum is consistent with the theoretical XRD spectrum, which proves the existence of the compound guanidinium tetrafluoroborate.

Said hydrothermal method was used to grow nonlinear optical crystal of guanidinium tetrafluoroborate, and the specific operation was carried out according to the following steps:

a. Guanidinium carbonate and tetrafluoroboric acid were fully mixed and grinded in a molar ratio of $NH_2:BF_4=3:1$, then 10 mL of deionized water was added to mix and dissolve the mixture thoroughly;

b. The mixture solution of step a was transferred into the polytetrafluoroethylene lining of an autoclave reactor with a volume of 25 mL, then the reactor was sealed tightly;

c. The autoclave reactor of step b was placed in an incubator; the incubator was heated up to 50° C. at a rate of 20° C./h and kept at this temperature constantly for 3 days, then the temperature was reduced to room temperature at a cooling rate of 10° C./day;

d. The autoclave reactor was opened, and nonlinear optical crystal of guanidinium tetrafluoroborate in a size of 11×10×12 mm³ was obtained in a colorless clear solution.

Example 2

Said hydrothermal method was used to grow nonlinear optical crystal of guanidinium tetrafluoroborate, and the specific operation was carried out according to the following steps:

a. Guanidinium sulfate and lithium tetrafluoroborate were fully mixed and grinded in a molar ratio of $NH_2:BF_4=3:1$, then 50 mL of deionized water was added to mix and dissolve the mixture thoroughly;

b. The mixture solution of step a was transferred into the polytetrafluoroethylene lining of an autoclave reactor with a volume of 100 mL, then the reactor was sealed tightly;

c. The autoclave reactor of step b was placed in an incubator; the incubator was heated up to 230° C. at a rate of 60° C./h and kept at this temperature constantly for 15 days, then the temperature was reduced to room temperature at a cooling rate of 100° C./day;

d. The autoclave reactor was opened, and nonlinear optical crystal of guanidinium tetrafluoroborate in a size of 18×20×33 mm³ was obtained in a colorless clear solution.

Example 3

Said hydrothermal method was used to grow nonlinear optical crystal of guanidinium tetrafluoroborate, and the specific operation was carried out according to the following steps:

a. Guanidinium nitrate and ammonium tetrafluoroborate were fully mixed and grinded in a molar ratio of $NH_2:BF_4=3:1$, then 40 mL of deionized water was added to mix and dissolve the mixture thoroughly;

b. The mixture solution of step a was transferred into the polytetrafluoroethylene lining of an autoclave reactor with a volume of 70 mL, then the reactor was sealed tightly;

c. The autoclave reactor of step b was placed in an incubator; the incubator was heated up to 150° C. at a rate of 40° C./h and kept at this temperature constantly for 7 days, then the temperature was reduced to room temperature at a cooling rate of 60° C./day;

d. The autoclave reactor was opened, and nonlinear optical crystal of guanidinium tetrafluoroborate in a size of 11×22×23 mm³ was obtained in a colorless clear solution.

Example 4

Said hydrothermal method was used to prepare nonlinear optical crystal of guanidinium tetrafluoroborate, and the specific operation was carried out according to the following steps:

a. Guanidinium phosphate and sodium tetrafluoroborate were fully mixed and grinded in a molar ratio of $NH_2:BF_4=3:1$, then 10-50 mL of deionized water was added to mix and dissolve the mixture thoroughly;

b. The mixture solution of step a was transferred into the polytetrafluoroethylene lining of an autoclave reactor with a volume of 50 mL, then the reactor was sealed tightly;

c. The autoclave reactor of step b was placed in an incubator; the incubator was heated up to 200° C. at a rate of 50° C./h and kept at this temperature constantly for 7 days, then the temperature was reduced to room temperature at a cooling rate of 80° C./day;

d. The autoclave reactor was opened, and nonlinear optical crystal of guanidinium tetrafluoroborate in a centimeter-scaled large-size of 10×21×22 mm³ was obtained in a colorless clear solution.

Example 5

Said room temperature solution method was used to grow nonlinear optical crystal of guanidinium tetrafluoroborate, and the specific operation was carried out according to the following steps:

a. Guanidinium phosphate and sodium tetrafluoroborate were fully mixed and grinded in a molar ratio of $NH_2:BF_4=3:1$, then 10 mL of deionized water was added to mix and dissolve the mixture thoroughly;

b. The mixture solution of step a was transferred into a beaker with a volume of 50 mL; an ultrasonic treatment was conducted to make it fully mixed and dissolved; pH value of the solution was adjusted to 1; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 1 mm³ was obtained.

Example 6

Said room temperature solution method was used to grow nonlinear optical crystal of guanidinium tetrafluoroborate, and the specific operation was carried out according to the following steps:

a. Guanidinium sulfate and lithium tetrafluoroborate were fully mixed and grinded in a molar ratio of $NH_2:BF_4=3:1$, then 200 mL of deionized water was added to mix and dissolve the mixture thoroughly;

b. The mixture solution of step a was transferred into a beaker with a volume of 300 mL; an ultrasonic treatment was conducted to make it fully mixed and dissolved; pH value of the solution was adjusted to 11; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 20 mm$^3$ was obtained.

Example 7

Said room temperature solution method was used to grow nonlinear optical crystal of guanidinium tetrafluoroborate, and the specific operation was carried out according to the following steps:
  a. Guanidinium nitrate and lithium tetrafluoroborate were fully mixed and grinded in a molar ratio of $NH_2:BF_4=3:1$, then 100 mL of deionized water was added to mix and dissolve the mixture thoroughly;
  b. The mixture solution of step a was transferred into a beaker with a volume of 200 mL; an ultrasonic treatment was conducted to make it fully mixed and dissolved; pH value of the solution was adjusted to 5; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 12 mm$^3$ was obtained.

Example 8

Said room temperature solution method was used to prepare nonlinear optical crystal of guanidinium tetrafluoroborate, and the specific operation was carried out according to the following steps:
  a. Guanidinium carbonate and sodium tetrafluoroborate were fully mixed and grinded in a molar ratio of $NH_2:BF_4=3:1$, then 10-200 mL of deionized water was added to mix and dissolve the mixture thoroughly;
  b. The mixture solution of step a was transferred into a beaker with a volume of 150 mL; an ultrasonic treatment was conducted to make it fully mixed and dissolved; pH value of the solution was adjusted to 10; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 15 mm$^3$ was obtained.

Example 9

Said evaporation method was used to grow nonlinear optical crystal of guanidinium tetrafluoroborate, and the specific operation was carried out according to the following steps:
  a. Guanidinium nitrate and tetrafluoroboric acid were fully mixed and grinded in a molar ratio of $NH_2:BF_4=3:1$, then 10 mL of deionized water was added to mix and dissolve the mixture thoroughly;
  b. The mixture solution of step a was transferred into a beaker with a volume of 50 mL; an ultrasonic treatment was conducted to make it fully mixed and dissolved; the solution was filtered through qualitative filter paper;
  c. The beaker of step b was placed in an incubator; the incubator was heated up to 50° C. at a rate of 5° C./h and then kept at this temperature constantly for 3 days; when the growth ended, nonlinear optical crystal of guanidinium tetrafluoroborate in a size of 1 mm$^3$ was obtained.

Example 10

Said evaporation method was used to grow nonlinear optical crystal of guanidinium tetrafluoroborate, and the specific operation was carried out according to the following steps:
  a. Guanidinium sulfate and ammonium tetrafluoroborate were fully mixed and grinded in a molar ratio of $NH_2:BF_4=3:1$, then 200 mL of deionized water was added to mix and dissolve the mixture thoroughly;
  b. The mixture solution of step a was transferred into a beaker with a volume of 300 mL; an ultrasonic treatment was conducted to make it fully mixed and dissolved; the solution was filtered through qualitative filter paper;
  c. The beaker of step b was placed in an incubator; the incubator was heated up to 120° C. at a rate of 10° C./h and then kept at this temperature constantly for 15 days; when the growth ended, nonlinear optical crystal of guanidinium tetrafluoroborate in a size of 20 mm$^3$ was obtained.

Example 11

Said evaporation method was used to grow nonlinear optical crystal of guanidinium tetrafluoroborate, and the specific operation was carried out according to the following steps:
  a. Guanidinium carbonate and sodium tetrafluoroborate were fully mixed and grinded in a molar ratio of $NH_2:BF_4=3:1$, then 120 mL of deionized water was added to mix and dissolve the mixture thoroughly;
  b. The mixture solution of step a was transferred into a beaker with a volume of 250 mL; an ultrasonic treatment was conducted to make it fully mixed and dissolved; the solution was filtered through qualitative filter paper;
  c. The beaker of step b was placed in an incubator; the incubator was heated up to 100° C. at a rate of 10° C./h and then kept at this temperature constantly for 13 days; when the growth ended, nonlinear optical crystal of guanidinium tetrafluoroborate in a size of 14 mm$^3$ was obtained.

Example 12

Said evaporation method was used to grow nonlinear optical crystal of guanidinium tetrafluoroborate, and the specific operation was carried out according to the following steps:
  a. Guanidinium phosphate and lithium tetrafluoroborate were fully mixed and grinded in a molar ratio of $NH_2:BF_4=3:1$, then 10-200 mL of deionized water was added to mix and dissolve the mixture thoroughly;
  b. The mixture solution of step a was transferred into a beaker with a volume of 180 mL; an ultrasonic treatment was conducted to make it fully mixed and dissolved; the solution was filtered through qualitative filter paper;

c. The beaker of step b was placed in an incubator; the incubator was heated up to 100° C. at a rate of 8° C./h and then kept at this temperature constantly for 12 days; when the growth ended, nonlinear optical crystal of guanidinium tetrafluoroborate in a size of 12 mm$^3$ was obtained.

Example 13

Said solvothermal method was used to grow nonlinear optical crystal of guanidinium tetrafluoroborate, and the specific operation was carried out according to the following steps:
a. Guanidinium sulfate and lithium tetrafluoroborate were fully mixed and grinded in a molar ratio of $NH_2:BF_4=3:1$, then 10 mL of deionized water was added to mix and dissolve the mixture thoroughly;
b. The mixture solution of step a was transferred into a beaker with a volume of 50 mL; an ultrasonic treatment was conducted to make it fully mixed and dissolved; pH value of the solution was adjusted to 1; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 10 mm$^3$ was obtained.

Example 14

Said solvothermal method was used to prepare nonlinear optical crystal of guanidinium tetrafluoroborate, and the specific operation was carried out according to the following steps:
a. Guanidinium carbonate and sodium tetrafluoroborate were fully mixed and grinded in a molar ratio of $NH_2:BF_4=3:1$, then 50 mL of absolute ethanol was added to mix and dissolve the mixture thoroughly;
b. The mixture solution of step a was transferred into a beaker with a volume of 200 mL; an ultrasonic treatment was conducted to make it fully mixed and dissolved; pH value of the solution was adjusted to 11; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 1 mm$^3$ was obtained.

Example 15

Said solvothermal method was used to prepare nonlinear optical crystal of guanidinium tetrafluoroborate, and the specific operation was carried out according to the following steps:
a. Guanidinium sulfate and ammonium tetrafluoroborate were fully mixed and grinded in a molar ratio of $NH_2:BF_4=3:1$, then 10 mL of hydrofluoric acid was added to mix and dissolve the mixture thoroughly;
b. The mixture solution of step a was transferred into a beaker with a volume of 300 mL; an ultrasonic treatment was conducted to make it fully mixed and dissolved; pH value of the solution was adjusted to 7; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 20 mm$^3$ was obtained.

Example 16

Said solvothermal method was used to prepare nonlinear optical crystal of guanidinium tetrafluoroborate, and the specific operation was carried out according to the following steps:
a. Guanidinium carbonate and lithium tetrafluoroborate were fully mixed and grinded in a molar ratio of $NH_2:BF_4=3:1$, then 10 mL of tetrafluoroboric acid was added to mix and dissolve the mixture thoroughly;
b. The mixture solution of step a was transferred into a beaker with a volume of 170 mL; an ultrasonic treatment was conducted to make it fully mixed and dissolved; pH value of the solution was adjusted to 10; the solution was filtered through qualitative filter paper, sealed with polyvinyl chloride film and placed in a static environment with no shaking, no pollution, and no air convection; a number of small holes were poked on the seal to adjust the volatilization rate of the solvent in the solution; then the solution was kept at room temperature; when the growth ended, nonlinear optical crystal of guanidinium tetrafluoroborate in a size of 13 mm$^3$ was obtained.

Example 17

Figure 2:
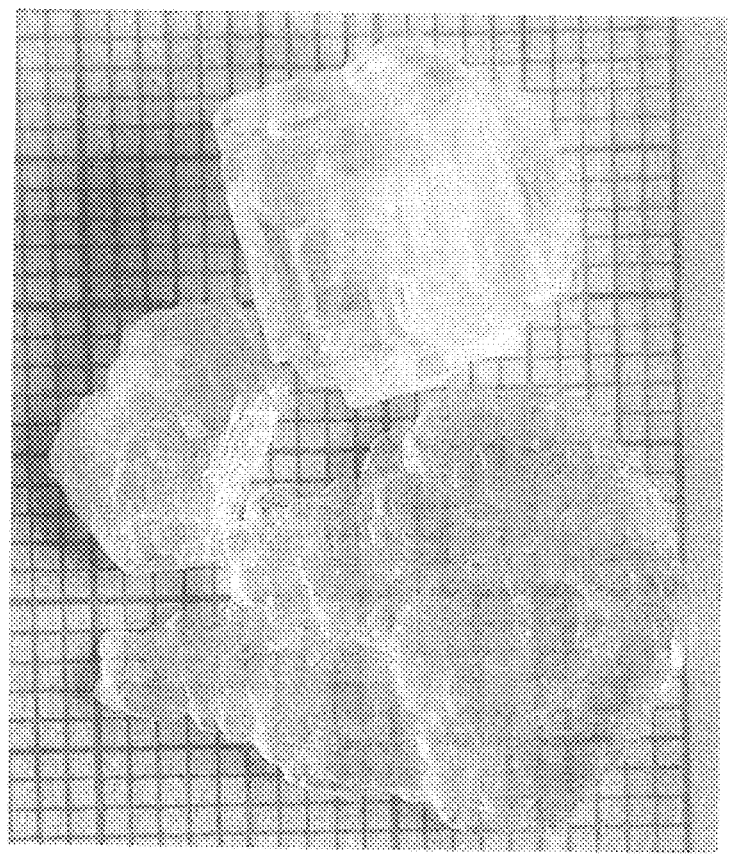
FIG. 2 is the photogram of nonlinear optical crystal of guanidinium tetrafluoroborate of the present invention.
Figure 3:
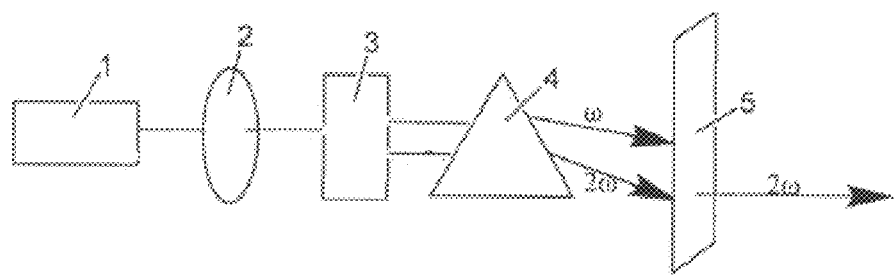
FIG. 3 is the functional diagram of a nonlinear optical device made of a nonlinear optical crystal of guanidinium tetrafluoroborate according to the present invention, wherein 1 represents a laser, 2 represents an emission light beam, 3 represents the nonlinear optical crystal of guanidinium tetrafluoroborate, and 4 represents an emergent light beam, and 5 represents a filter.

Any nonlinear optical crystal of guanidinium tetrafluoroborate $[C(NH_2)_3]BF_4$ (FIG. 2) obtained in Examples 1-16 was processed in the matching direction, and placed at the position 3 as shown in FIG. 3. At room temperature, a Q-switched Nd:YAG laser was used as the light source; and the incident wavelength was 1064 nm. An infrared light beam 2 with a wavelength of 1064 nm was emitted from the Q-switched Nd:YAG laser 1 and entered the $C(NH_2)_3]BF_4$ monocrystal 3 to generate a green frequency-multiplication light with a wavelength of 532 nm. And its output intensity was about 4.3 times of that of KDP under the same conditions.

Example 18

Any nonlinear optical crystal of guanidinium tetrafluoroborate $[C(NH_2)_3]BF_4$ (FIG. 2) obtained in Examples 1-16 was processed in the matching direction, and placed at the position 3 as shown in FIG. 3. At room temperature, a Q-switched Nd:YAG laser was used as the light source; and the incident wavelength was 532 nm. An infrared light beam 2 with a wavelength of 532 nm was emitted from the Q-switched Nd:YAG laser 1 and entered the $[C(NH_2)_3]BF_4$ monocrystal 3 to generate a frequency-multiplication light with a wavelength of 266 nm. And its output intensity was about 1.2 times of that of BBO under the same conditions.

The invention claimed is:
1. A nonlinear optical crystal of guanidinium tetrafluoroborate, wherein the crystal has a chemical formula of $[C(NH_2)_3]BF_4$ and a molecular weight of 146.89;

the crystal belongs to the trigonal crystal system;

the crystal has a space group of R3m;

the crystal has lattice parameters of a=7.4634(10)Å, b=7.4634(10)Å, c=9.1216(19) (6)Å, Z=3; and the crystal has an ultraviolet cut-off edge below 200 nm.

2. A method for preparing the nonlinear optical crystal of guanidinium tetrafluoroborate according to claim 1, wherein a hydrothermal method, a room temperature solution method, an evaporation method or a solvothermal method is utilized to prepare the crystal;

wherein the hydrothermal method for preparing the nonlinear optical crystal of guanidinium tetrafluoroborate comprises:

a. mixing a $NH_2$ group-containing compound and a $BF_4$ group-containing compound in a molar ratio of $NH_2$:$BF_4$=3:1, and fully grinding the compounds, then adding 10-50 mL of deionized water to mix and dissolve the compounds thoroughly and form a mixture solution;

wherein the $NH_2$ group-containing compound is one or more of guanidinium carbonate, guanidinium sulfate, guanidinium nitrate and guanidinium phosphate, and the $BF_4$ group-containing compound is one or more of tetrafluoroboric acid, ammonium tetrafluoroborate, lithium tetrafluoroborate and sodium tetrafluoroborate;

b. transferring the mixture solution of the step a into a polytetrafluoroethylene lining of an autoclave reactor with a volume of 25-100 mL, and sealing the autoclave reactor tightly;

c. placing the autoclave reactor of step b in an incubator, and heating up the incubator to 50-230° C. at a rate of 20-60° C./hour, keeping the incubator at the temperature constantly for 3-15 days, and then reducing the temperature to room temperature at a cooling rate of 10-100° C./day; and d. opening the autoclave reactor, and obtaining a centimeter-scale large-size nonlinear optical crystal of guanidinium tetrafluoroborate in a colorless clear solution;

the room temperature solution method for preparing the nonlinear optical crystal of guanidinium tetrafluoroborate comprises:

a. mixing a $NH_2$ group-containing compound and a $BF_4$ group-containing compound in a molar ratio of $NH_2$:$BF_4$=3:1, fully grinding the compounds, then adding 10-200 mL deionized water to mix and dissolve the compounds thoroughly to obtain a mixture solution;

wherein the $NH_2$ group-containing compound is one or more of guanidinium carbonate, guanidinium sulfate, guanidinium nitrate and guanidinium phosphate, and the $BF_4$ group-containing compound is one or more of tetrafluoroboric acid, ammonium tetrafluoroborate, lithium tetrafluoroborate and sodium tetrafluoroborate; and b. transferring the mixture solution of step a into a beaker with a volume of 50-300 mL, conducting an ultrasonic treatment to make the mixture solution fully mixed and dissolved, adjusting pH value of the solution to 1-11, filtering the solution through qualitative filter paper, and then sealing the beaker with polyvinyl chloride film, placing the sealed beaker in a static environment with no shaking, no pollution, and no air convection, poking a number of small holes on the seal to adjust the volatilization rate of the solvent in the solution, and keeping the beaker at room temperature until the growth ends, then obtaining nonlinear optical crystal of guanidinium tetrafluoroborate in a size of 1-20 $mm^3$;

the evaporation method for preparing the nonlinear optical crystal of guanidinium tetrafluoroborate comprises:

a. mixing a $NH_2$ group-containing compound and a $BF_4$ group-containing compound in a molar ratio of $NH_2$:$BF_4$=3:1, fully grinding the compounds, then adding 10-200 mL deionized water to mix and dissolve the compounds thoroughly to form a mixture solution;

wherein the $NH_2$ group-containing compound is one or more of guanidinium carbonate, guanidinium sulfate, guanidinium nitrate and guanidinium phosphate, and the $BF_4$ group-containing compound is one or more of tetrafluoroboric acid, ammonium tetrafluoroborate, lithium tetrafluoroborate and sodium tetrafluoroborate;

b. transferring the mixture solution of step a into a beaker with a volume of 50-300 mL, conducting an ultrasonic treatment to make the mixture solution fully mixed and dissolved, and filtering the solution through qualitative filter paper; and c. placing the beaker of step b in an incubator, and heating up the incubator to 50-120° C. at a rate of 5-10° C./h, keeping the beaker at the temperature constantly for 3-15 days until the growth ends, then obtaining nonlinear optical crystal of guanidinium tetrafluoroborate in a size of 1-20 $mm^3$; and the solvothermal method for preparing the nonlinear optical crystal of guanidinium tetrafluoroborate comprises:

a. mixing a $NH_2$ group-containing compound and a $BF_4$ group-containing compound in a molar ratio of $NH_2$:$BF_4$=3:1, fully grinding the compounds, then adding 10-200 mL solvent to mix and dissolve the compounds thoroughly to form a mixture solution;

wherein the $NH_2$ group-containing compound is one or more of guanidinium carbonate, guanidinium sulfate, guanidinium nitrate and guanidinium phosphate; the $BF_4$ group-containing compound is one or more of tetrafluoroboric acid, ammonium tetrafluoroborate, lithium tetrafluoroborate and sodium tetrafluoroborate; and the solvent is deionized water, absolute ethanol, hydrofluoric acid or tetrafluoroboric acid; and b. transferring the mixture solution of step a into a beaker with a volume of 50-300 mL, conducting an ultrasonic treatment to make the mixture solution fully mixed and dissolved, adjusting pH value of the solution to 1-11, filtering the solution through qualitative filter paper, and then sealing the beaker with polyvinyl chloride film, placing the sealed beaker in a static environment with no shaking, no pollution, and no air convection, poking a number of small holes on the seal to adjust the volatilization rate of the solvent in the solution, and keeping the beaker at room temperature until the growth ends, then obtaining nonlinear optical crystal of guanidinium tetrafluoroborate in a size of 1-20 $mm^3$.

3. A device selected from the group consisting of multi-band frequency-multiplication devices or optical elements, wherein the device includes the nonlinear optical crystal of guanidinium tetrafluoroborate according to claim 1.

4. The device according to claim 3, wherein the device is a frequency-multiplication generator, a frequency up or down converter, or an optical parametric oscillator.

5. A method of producing frequency-doubling, frequency-tripling, frequency-quadrupling, frequency-quintupling or frequency-sextupling harmonic light output comprising applying fundamental frequency light of 1064 nm generated by a Nd:YAG laser to the nonlinear optical crystal of guanidinium tetrafluoroborate according to claim 1.

6. The nonlinear optical crystal of guanidinium tetrafluoroborate according to claim 1, wherein the crystal is capable of producing a deep ultraviolet frequency-multiplication light output below 200 nm.

7. The nonlinear optical crystal of guanidinium tetrafluoroborate according to claim 1, wherein the crystal has a size of 1-20 mm$^3$.

* * * * *